United States Patent [19]

Bänziger et al.

[11] Patent Number: 5,254,756
[45] Date of Patent: Oct. 19, 1993

[54] PROCESS FOR THE PRODUCTION OF (2R,3E)-4-HALO-3-BUTEN-2-OLS

[75] Inventors: Markus Bänziger, Brig-Glis; John McGarrity, Visp, both of Switzerland

[73] Assignee: Lonza Ltd., Basel, Switzerland

[21] Appl. No.: 971,564

[22] Filed: Nov. 5, 1992

[30] Foreign Application Priority Data

Nov. 15, 1991 [CH] Switzerland ............... 3339/91

[51] Int. Cl.$^5$ ............................................. C07C 33/42
[52] U.S. Cl. ................................. 568/843; 568/840; 568/841
[58] Field of Search ................... 568/840, 843, 841

[56] References Cited

PUBLICATIONS

F.-T. Luo and E.-I. Negishi, J. Org. Chem., 50 (1985), pp. 4762 to 4766.

T. Ito et al., Tetrahedron Lett., 30, (1989), pp. 7083 to 7086.
Y. Kitano et al., Tetrahedron Lett., 28, (1987), pp. 6351 to 6354.
W. B. Benson, J. Org. Chem., 29, (1964), p. 385.
Römpp Chemie-Lexikon, 9th Edition, vol. 5 (1992), p. 4135.

Primary Examiner—Werren B. Lone
Attorney, Agent, or Firm—Fisher, Christen & Sabol

[57] ABSTRACT

(2R,3E)-4-halo-3-buten-2-ols are produced by kinetic resolution of racemates from the corresponding racemates. The racemate is esterified by reaction with a carboxylic acid derivative, preferably with chloroacetyl chloride. Then the (R)-ester is enantioselectively hydrolyzed with a lipase from *Pseudomonas fluorescens*. The corresponding (2R,3E)-4-halo-3-buten-2-ol also can be obtained from the remaining (S)-ester after separation. The compounds are chiral synthesis structural elements for the production of optically active natural substances.

11 Claims, No Drawings

PROCESS FOR THE PRODUCTION OF (2R,3E)-4-HALO-3-BUTEN-2-OLS

BACKGROUND OF THE INVENTION

1. Field Of The Invention

The invention relates to a process for the production of (2R,3E)-4-halo-3-buten-2-ols from the corresponding racemic (2RS,3E)-4-halo-3-buten-2-ols.

2. Background Art

Optically-active secondary γ-haloallyl alcohols, especially the γ-iodoallyl alcohols, are valuable synthesis building blocks for the production of prostaglandins [see, e.g., F. -T. Luo and E. -I. Negishi, *J. Org. Chem.*, 50, (1985), 4762–4766] or of optically active propargyl alcohols, that on their part represent structural elements for various natural substances [see, e.g., T. Ito et al., *Tetrahedron Lett.*, 30. (1989), 7083–7086].

Since racemic γ-haloallyl alcohols are easily obtainable from carboxylic acid chlorides and acetylene via the corresponding chlorovinyl ketones [see, e.g., Y. Kitano et al., *Tetrahedron Lett.*, 28, (1987), 6351–6354], the optically active compounds are suitably produced by resolution of racemates. A known process in this connection is the kinetic resolution of racemates by epoxydation according to Sharpless in the presence of a chiral auxiliary substance (Y. Kitano et al., loc. cit.). Drawbacks of this process are the use of peroxy compounds that in large amounts represent a safety risk, as well as the fact that an enantiomer is lost by decomposing the epoxide formed from it in the subsequent working up.

BROAD DESCRIPTION OF THE INVENTION

The main objective of the invention is to provide a process for the production of (2R,3E)-4-halo-3-buten-2-ols, that does not require the use of peroxy compounds and that also allows use of the (2S)-enantiomer. Other objectives and advantages of the invention are set out herein or are obvious herefrom to one skilled in the art.

The objects and advantages of the invention are achieved by the process and compounds of the invention.

The invention involves a process for the production of (2R,3E)-4-halo-3-buten-2-ols from the corresponding racemic (2RS,3E)-4-halo-3-buten-2-ols by esterification and the enantioselective hydrolysis of the esters.

Regarding the invention, it was found that the esters that can be produced according to known methods from racemic (E)-4-halo-3-buten-2-ols of the general formula:

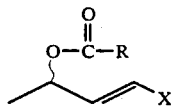

II wherein R is an alkyl group having 1 to 8 carbon atoms, optionally substituted with halogen, and X is chlorine, bromine or iodine, can be hydrolyzed enantioselectively with a lipase from *Pseudomonas fluorescens*. The unhydrolyzed (2S,3E)-ester, because of its different physical properties, can easily be separated from the hydrolysis product (2R,3E)-4-halo-3-buten-2-ol and then hydrolyzed to (2S,3E)-4-halo-3-buten-2-ol.

DETAILED DESCRIPTION OF THE INVENTION

Preferred esters are those of the carboxylic acids having 2 to 8 carbon atoms and their halogenated derivatives; and especially preferred are the esters of chloroacetic acid (R is chloromethyl).

Preferably the esters are produced by the reaction of racemic (E)-4-halo-3-buten-2-ol with the corresponding acid anhydride or acid chloride, for example, for the chloroacetic acid ester with chloroacetyl chloride in the presence of a tertiary amine, such as, triethylamine, to bind the resulting hydrogen chloride. Thus, advantageously an additional catalyst, such as, 4-(dimethylamino)pyridine, is used.

The enantioselective hydrolysis of the ester is performed according to the invention with a lipase from *Pseudomonas fluorescens*. Such lipases are commercially obtainable, for example, from Amano Pharmaceutical Co. Ltd., Nagoya, Japan, or Biocatalysts Ltd., Pontyprydd, U.K. Preferably the enantioselective hydrolysis is performed in a stirred two-phase system obtained from water and an organic solvent immiscible with water. Toluene is especially preferred as the organic solvent. The reaction temperature is suitably at 0° to 50° C., preferably 5° to 25° C.

To eliminate unwanted side reactions, the hydrolysis suitably is performed at a pH of 5 to 9, preferably at a pH of 6 to 8. Since the acid is liberated in the hydrolysis, the pH is suitably held constant by a buffer addition or preferably by an addition of a base taking place corresponding to the reaction progress. The base addition is preferably performed by a pH-measuring device and an automatic dosing apparatus (autotitrator). As the base, an aqueous alkali hydroxide solution is preferably used; and especially preferred is sodium hydroxide solution.

After the main amount of the (R)-ester is hydrolyzed, i.e., after a reaction of approximately 50 percent relative to the racemate, the reaction is terminated and the optically active alcohol is separated from the unreacted ester. The separation is advantageously performed by fractionating distillation under reduced pressure.

The following examples illustrate the performance of the process according to the invention.

EXAMPLE 1

(E)-4-iodo-3-buten-2-one 50 g (0.48 mol) of (E)-4-chloro-3-buten-2-one [produced according to W. B. Benson, *J. Org. Chem.*, 29, (1964), 385] was dissolved in 125 ml of acetone and stirred 1.8 hours at 60° C. under argon with 89.4 g (0.60 mol) of sodium iodide. Then the reaction mixture was concentrated by evaporation at 130 mbar and 35° C. bath temperature in a rotary evaporator. The residue was mixed with 150 ml of toluene and the thus-obtained suspension was washed with 150 ml of water. The aqueous phase was extracted three times with 100 ml of toluene each. The combined organic phases were dried on magnesium sulfate and concentrated by evaporation in a rotary evaporator. The yield was 85 g (crude product).

EXAMPLE 2

(2RS,3E)-4-iodo-3-buten-2-ol 85 g (0.43 mol) of (E)-4-iodo-3-buten-2-one (produced according to Example 1) was dissolved in 800 mol of toluene under argon. The solution was cooled to −10° C. and mixed, drop by drop, within 0.5 hour with 65 ml of a 3.5M solution of sodium dihydridobis(2-methoxyethoxy)aluminate in toluene. Then the mixture was first heated to room temperature, cooled to 0° C., and carefully mixed at this temperature first with 10 ml of methanol and then with 40 ml of 10 percent sodium hydroxide solution. The phases were separated and the aqueous phase was extracted with 200 ml of toluene. The toluene phase was washed once with 200 ml and twice with 100 ml of water, then dried on magnesium sulfate and concentrated by evaporation in a rotary evaporator. The yield was 67.7 g [crude product, content (GC) 85 percent]. Further data on the product is:

$^1$H-NMR: (CDCl$_3$, 300 MHz) δ1.3 (d, 3H); 2.05 (br.d), 1H); 4.23–4.36 (m, 1H); 6.35 (d, 1H); 6.62 (dd, 1H).

EXAMPLE 3

Chloroacetic acid-(2RS,3E)-4-iodo-3-buten-2-yl ester 57.1 g (0.25 mol) of (2RS,3E)-4-iodo-3-buten-2-ol (86 percent, produced according to Example 2) was dissolved in 400 ml of toluene under argon, cooled to 0° C. and mixed with 2.4 g (20 mmol) of 4-(dimethylamino)-pyridine. Then the mixture was cooled to −5° C., mixed with 11.07 g of triethylamine and cooled again to −10° C. After drop-by-drop addition of a first portion of 12.4 g of chloroacetyl chloride within 15 minutes (exothermic reaction) and another 0.5 hour of stirring, the same amounts of triethylamine and chloroacetyl chloride were instilled in succession. Again after 0.5 hour finally a third portion each was instilled, thus, altogether there were 33.21 g of triethylamine and 37.2 g chloroacetyl chloride added. Triethylammonium chloride precipitated during the addition of chloroacetyl chloride. After the final addition the mixture was stirred 1.5 hours more at −5° C. and then heated to room temperature. After another 3 hours the triethylammonium chloride was filtered off and washed with toluene. The filtrate was washed twice with 80 ml of 0.1M hydrochloric acid each. The aqueous phase was reextracted once with 50 ml of toluene. The combined organic phases were dried on magnesium sulfate, filtered and concentrated by evaporation on a rotary evaporator. The yield was 72.4 g (crude product, still contains some toluene). Further data on the product is:

$^1$H-NMR (CDCl$_3$, 300 MHz) δ1.38 (d, 3H); 4.05 (s, 2H); 5.30–5.43 (m, 1H); 6.50–6.58 (m, 2H).

EXAMPLE 4

(2R,3E)-4-iodo-3-buten-2-ol 72 g of chloroacetic acid-(2RS,3E)-4-iodo-3-buten-2-yl ester (produced according to Example 3) was dissolved in 136 ml of toluene. The solution was stirred at room temperature with 680 ml of water and 680 mg of lipase PS (from *Pseudomonas fluorescens*, manufacturer: Amano), and the pH measured with a glass electrode and held constant at 7 by the addition of 1M sodium hydroxide solution by an autotitrator. After 2.5 hours the reaction was terminated. The reaction mixture was filtered through Celite ®, mixed with an additional 160 ml of toluene and shaken. After separation of the phases the aqueous phase was extracted twice more with 160 ml of toluene each. The combined organic phases were dried on magnesium sulfate, filtered and concentrated by evaporation on a rotary evaporator. The crude product thus obtained (57.4 g) was rectified by means of a split-tube column. The yield was 16.65 g [corresponding to 34 percent, relative to racemic (E)4-iodo-3-buten-2-ol, or 68 percent of theory. Regarding the product, the content (GC)≃100 percent and the optical purity (ee value):>99 percent.

What is claimed is:

1. A process for the production of a (2R, 3E)-4-halo-3-buten-2-ol of the formula:

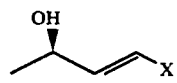   I where X is chlorine, bromine or iodine, from the corresponding racemic (2RS,3E)-4-halo-3-buten-2-ol, comprising reacting the racemic (2RS,3E)-4-halo-3-buten-2-ol with the corresponding acid anhydride or acid chloride in the presence of a tertiary amine into a corresponding racemic ester having the formula:

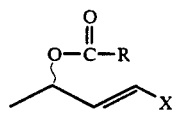   II wherein R is selected from the group consisting of an alkyl group having 1 to 8 carbon atoms, and an alkyl group having 1 to 8 carbon atoms and being substituted with halogen, and X has the above mentioned meaning, and then enantioselectively hydrolyzing the corresponding racemic ester of formula II with a lipase from *Pseudomonas fluorescens*.

2. The process according to claim 1 wherein R is chloromethyl.

3. The process according to claim 2 wherein the racemic ester is produced by reaction of the racemic (2RS,3E)-4-halo-3-buten-2-ol with chloroacetyl chloride in the presence of a tertiary amine.

4. The process according to claim 3 wherein the tertiary amine is triethylamine.

5. The process according to claim 4 wherein 4-(dimethylamino)pyridine is also present as an additional catalyst.

6. The process according to claim 5 wherein the enantioselective hydrolysis is performed in a two phase system from water and an organic solvent immiscible with water.

7. The process according to claim 6 wherein the enantioselective hydrolysis is performed at a pH of 6 to 8.

8. The process according to claim 7 wherein X is iodine.

9. The process according to claim 1 wherein the enantioselective hydrolysis is performed in a two phase system form water and an organic immiscible with water.

10. The process according to claim 1 wherein the enantioselective hydrolysis is performed at a pH of 6 to 8.

11. The process according to claim 1 wherein X is iodine.

* * * * *